United States Patent [19]
Fukuda et al.

[11] Patent Number: 5,714,349
[45] Date of Patent: Feb. 3, 1998

[54] SYNTHETIC GENE CODING FOR HUMAN PARATHYROID HORMONE

[75] Inventors: Tsunehiko Fukuda, Kyoto; Yuri Oshika; Takao Yamada, both of Osaka, all of Japan

[73] Assignee: Takeda Chemical Industries, Ltd., Osaka, Japan

[21] Appl. No.: 689,190

[22] Filed: Aug. 5, 1996

Related U.S. Application Data

[63] Continuation of Ser. No. 6,197, Jan. 19, 1993, abandoned, which is a continuation of Ser. No. 765,371, Sep. 25, 1991, abandoned.

[30] Foreign Application Priority Data

Sep. 28, 1990 [JP] Japan .................................. 2-257491
Mar. 20, 1991 [JP] Japan .................................. 3-056434

[51] Int. Cl.[6] ............................. C12P 21/06; C12N 1/21; C12N 15/16; C07H 17/00
[52] U.S. Cl. ................. 435/69.4; 435/252.3; 435/320.1; 536/23.51
[58] Field of Search ...................... 536/23.51; 435/69.4, 435/320.1, 71.2, 252.33, 69.7, 252.3; 526/23.1, 23.5

[56] References Cited

U.S. PATENT DOCUMENTS 5,010,010  4/1991  Gautvik et al. .......................... 435/252.3

FOREIGN PATENT DOCUMENTS 0178863     4/1986  European Pat. Off. .
WO 88/03165 5/1988  WIPO .
WO91/05050  4/1991  WIPO .

OTHER PUBLICATIONS

Hogset, et al., The Journal of Biological Chemistry, 265:7338–7344 (1990).
Rabbani, et al., The Journal of Biological Chemistry, 263:1307–1313 (1988).
Sung, et al., Biochemistry and Cell Biology, 64:133–138 (1986).
Sung, et al., The Journal of Biological Chemistry, 266:2831–2835 (1991).
Gabrielsen, et al., Gene, 90:255–262 (1990).
Sung, et al., Gene, 47:261–267 (1986).
Ernst, TIBTECH Aug. 1988 vol. 6, pp. 196–199.
Carrier et al, Trends in Bio technology vol. 1, (4) 1983, pp. 109–113.
Robinson et al, N.A. Res. 12(17) 1984, pp. 6663–6671.
Grosjean, Gene 18, 1982, pp. 199–209.
Sharp et al N.A. Res. 15(3) 1987, pp. 1281–1295.
Holm, N.A. Res. 14(7) 1986, pp. 3075–3087.
Das, Methods Enzymology v 182, 1990, pp. 93–112.
Ferretti et al PNAS 83, 1986, pp. 599–603.
Snyder et al. (1987) Methods in Enzymology, vol. 154, pp. 107–128.
Hendy et al. 1981 PNAS 78(12): 7365–7369.
Sanbrook et al 1989 Molecular Cloning A Laboratory Manual CSHL, CSH, NY pp. 8.36–8.38, 17.11–17.16.

*Primary Examiner*—Karen C. Carlson
*Attorney, Agent, or Firm*—David G. Conlin; David S. Resnick; Dike, Bronstein, Roberts & Cushman, LLP

[57] ABSTRACT

Disclosed are (1) a DNA containing a synthetic gene for expression of human parathyroid hormone represented by the following DNA sequence:

TCTGTG TCCGAGATTC AGTTAATGCA TAACCT-
TGGC AAACATTTGA ACTCCATGGA GCGTGTA-
GAA TGGCTGCGTA AGAAGTTGCA GGATGTG-
CAC    AATTTTGTTG    CCTTAGGTGC
CCCATTGGCT CCTCGTGATG CTGGTTCCCA
AAGACCACGT AAAAAGGAAG ACAATGTCTT
AGTTGAGAGC CATGAAAAAT CCCTAGGCGA
GGCAGACAAG GCCGATGTGA ATGTATTAAC
TAAAGCTAAA TCCCAG (2) a method for producing the DNA described in (1), which comprises enzymatically ligating a plurality of oligodeoxynucleotides to one another to form the DNA and inserting the DNA into a vector if necessary, (3) a transformant transformed by the DNA described in (1), and (4) a method for producing human parathyroid hormone which comprises cultivating the transformant described in (3), accumulating human parathyroid hormone in a culture medium, and collecting the same, whereby hPTH can be allowed to express in large amounts in a system using *E. coli* as a host.

3 Claims, 7 Drawing Sheets

TCT.GTG.TCC.GAG.ATT.CAG.TTA.ATG.CAT.AAC.CTT.GCC.AAA.CAT.TTG.AAC.TCC.ATG.GAG
Ser-Val-Ser-Glu-Ile-Gln-Leu-Met-His-Asn-Leu-Gly-Lys-His-Leu-Asn-Ser-MET-Glu

CGT.GTA.GAA.TGG.CTC.CGT.AAG.AAG.TTG.CAG.GAT.GTG.CAC.AAT.TTT.GTT.GCC.TTA.GGT.GCC
Arg-Val-Glu-Trp-Leu-Arg-Lys-Lys-Leu-Gln-Asp-Val-His-Asn-Phe-Val-Ala-Leu-Gly-Ala

CCA.TTG.CCT.CCT.CGT.GAT.GCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

FIG. 1

```
       10         20         30         40         50         60
TATGTCTGTG  TCCGAGATTC  AGTTAATGCA  TAACCTTGGC  AAACATTTGA  ACTCCATGGA
 ACAGACAC   AGGCTCTAAG  TCAATTACGT  ATTGGAACCG  TTTGTAAACT  TGAGGTACCT
Nde I           Hinf I                                           Nco I 70         80         90        100        110        120
GCGTGTAGAA  TGGCTGCGTA  AGAAGTTGCA  GGATGTGCAC  AATTTTGTTG  CCTTAGGTGC
CGCACATCTT  ACCGACGCAT  TCTTCAACGT  CCTACACGTG  TTAAAACAAC  GGAATCCACG
                          HgiA I                              Dde I 130        140        150        160        170        180
CCCATTGGCT  CCTCGTGATG  CTGGTTCCCA  AAGACCACGT  AAAAAGGAAG  ACAATGTCTT
GGGTAACCGA  GGAGCACTAC  GACCAAGGGT  TTCTGGTGCA  TTTTTCCTTC  TGTTACAGAA
  Bgℓ I                                                         Dde I 190        200        210        220        230        240
AGTTGAGAGC  CATGAAAAAT  CCCTAGGCGA  GGCAGACAAG  GCCGATGTGA  ATGTATTAAC
TCAACTCTCG  GTACTTTTTA  GGGATCCGCT  CCGTCTGTTC  CGGCTACACT  TACATAATTG
                          Avr II                 HaeIII 250        260        270
TAAAGCTAAA  TCCCAGTAAT  GAG
ATTTCGATTT  AGGGTCATTA  CTCCTAG
  Alu I                  BamH I
```

FIG. 2

1  5'TATGTCTGTGTCCGAGATTCAGTTAATGCA3'
2  3'ACAGACACAGGCTCTAAGTCAATTACGTATTGGA5'

3  5'TAACCTTGGCAAACATTTGAACTCCATGGAGCGTGTAGAATGGCT3'
4  3'ACCGTTTGTAAACTTGAGGTACCTCGCACATCTTACCGACGCATT5'

5  5'GCGTAAGAAGTTGCAGGATGTGCACAATTT3'
6  3'CTTCAACGTCCTACACGTGTTAAAACAACG5'

7  5'TGTTGCCCTTAGGTGCCCCATTGGCTCCTCCTGATGCTGGTTCCCAA3'
8  3'GAATCCACGGGGTAACCGAGGAGGACTACGACCAAGGGTTTCTGGT5'

9  5'AGACCACGTAAAAAGGAAGAACAATGTCTTAGTTGAGAGCCCA3'
10 3'GCATTTTTCCTTCTTGTTACAGAATCAACTCTCGGTACTTTT5'

11 5'TGAAAAATCCCTAGGCCGAGGCAGAGACAAGGCCCGATGTGAATGT3'
12 3'TAGGGATCCGGCTCCGTCTCTGTTCCGGCTACACTTACATAATTG5'

13 5'ATTAACTAAAGCTAAATCCCAGTAATGAG3'
14 3'ATTTCGATTTAGGGTCATTACTCCTAG5'

FIG. 3

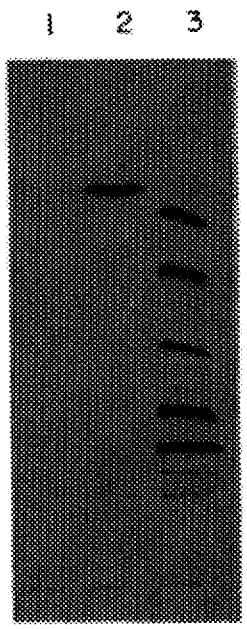
F I G. 9
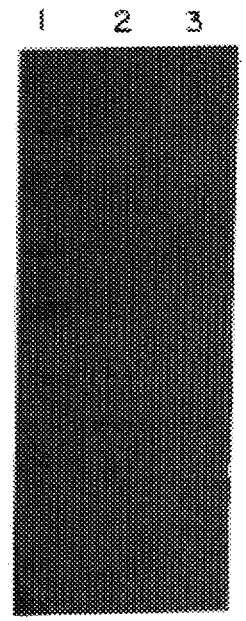
F I G. 10
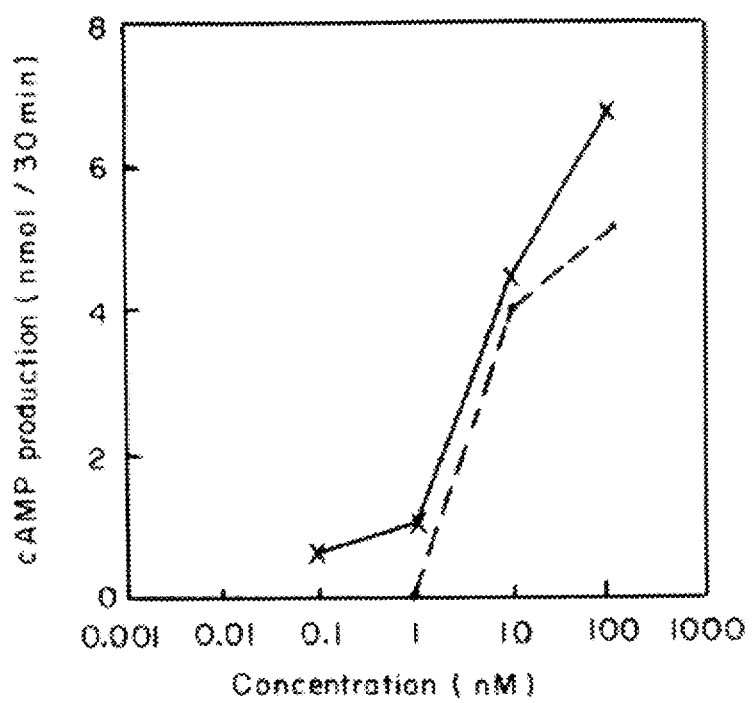
F I G. 11

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 252 base pairs
( B ) TYPE: nucleic acid
( C ) STRANDEDNESS: double
( D ) TOPOLOGY: linear ( i i ) MOLECULE TYPE: other nucleic acid, synthesizing DNA ( i x ) FEATURE:
  ( A ) NAME/KEY: CDS
  ( B ) LOCATION: 1..252
  ( C ) IDENTIFICATION METHOD:E ( i x ) FEATURE:
  ( A ) NAME/KEY: MUTATION
  ( B ) LOCATION: 7, 8, 9, 12, 15, 19, 21, 33, 36, 43, 51, 58, 60,
       82, 109, 111, 114, 117, 120, 121, 123, 129, 130, 132,
       147, 150, 153, 156, 177, 196, 197, 198, 201, 204, 216,
       219
  ( C ) IDENTIFICATION METHOD:S ( x i ) SEQUENCE DESCRIPTION: SEQ ID NO:1:

| | | | | | | | | | | | | | | | | |
|---|---|---|---|---|---|---|---|---|---|---|---|---|---|---|---|---|
| TCT | GTG | TCC | GAG | ATT | CAG | TTA | ATG | CAT | AAC | CTT | GGC | AAA | CAT | TTG | AAC | 48 |
| Ser | Val | Ser | Glu | Ile | Gln | Leu | Met | His | Asn | Leu | Gly | Lys | His | Leu | Asn | |
| 1 | | | | 5 | | | | | 10 | | | | | 15 | | |
| TCC | ATG | GAG | CGT | GTA | GAA | TGG | CTG | CGT | AAG | AAG | TTG | CAG | GAT | GTG | CAC | 96 |
| Ser | Met | Glu | Arg | Val | Glu | Trp | Leu | Arg | Lys | Lys | Leu | Gln | Asp | Val | His | |
| | | | 20 | | | | | 25 | | | | | 30 | | | |
| AAT | TTT | GTT | GCC | TTA | GGT | GCC | CCA | TTG | GCT | CCT | CGT | GAT | GCT | GGT | TCC | 144 |
| Asn | Phe | Val | Ala | Leu | Gly | Ala | Pro | Leu | Ala | Pro | Arg | Asp | Ala | Gly | Ser | |
| | | 35 | | | | | 40 | | | | | 45 | | | | |
| CAA | AGA | CCA | CGT | AAA | AAG | GAA | GAC | AAT | GTC | TTA | GTT | GAG | AGC | CAT | GAA | 192 |
| Gln | Arg | Pro | Arg | Lys | Lys | Glu | Asp | Asn | Val | Leu | Val | Glu | Ser | His | Glu | |
| | 50 | | | | | 55 | | | | | 60 | | | | | |
| AAA | TCC | CTA | GGC | GAG | GCA | GAC | AAG | GCC | GAT | GTG | AAT | GTA | TTA | ACT | AAA | 240 |
| Lys | Ser | Leu | Gly | Glu | Ala | Asp | Lys | Ala | Asp | Val | Asn | Val | Leu | Thr | Lys | |
| 65 | | | | | 70 | | | | | 75 | | | | | 80 | |
| GCT | AAA | TCC | CAG | | | | | | | | | | | | | 252 |
| Ala | Lys | Ser | Gln | | | | | | | | | | | | | |

( 2 ) INFORMATION FOR SEQ ID NO:2:

( i ) SEQUENCE CHARACTERISTICS:
    ( A ) LENGTH: 84 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Ser | Val | Ser | Glu | Ile | Gln | Leu | Met | His | Asn | Leu | Gly | Lys | His | Leu | Asn |
| 1 | | | | 5 | | | | | 10 | | | | | 15 | |
| Ser | Met | Glu | Arg | Val | Glu | Trp | Leu | Arg | Lys | Lys | Leu | Gln | Asp | Val | His |
| | | | 20 | | | | | 25 | | | | | 30 | | |
| Asn | Phe | Val | Ala | Leu | Gly | Ala | Pro | Leu | Ala | Pro | Arg | Asp | Ala | Gly | Ser |
| | | 35 | | | | | 40 | | | | | 45 | | | |
| Gln | Arg | Pro | Arg | Lys | Lys | Glu | Asp | Asn | Val | Leu | Val | Glu | Ser | His | Glu |
| | 50 | | | | | 55 | | | | | 60 | | | | |
| Lys | Ser | Leu | Gly | Glu | Ala | Asp | Lys | Ala | Asp | Val | Asn | Val | Leu | Thr | Lys |
| 65 | | | | | 70 | | | | | 75 | | | | | 80 |
| Ala | Lys | Ser | Gln | | | | | | | | | | | | |

( 2 ) INFORMATION FOR SEQ ID NO:3:

( i ) SEQUENCE CHARACTERISTICS:
    ( A ) LENGTH: 263 base pairs
    ( B ) TYPE: nucleic acid
    ( C ) STRANDEDNESS: double
    ( D ) TOPOLOGY: linear ( i i ) MOLECULE TYPE: other nucleic acid, synthesizing DNA ( i x ) FEATURE:
    ( A ) NAME/KEY: CDS (B) LOCATION: 2..262
(C) IDENTIFICATION METHOD:E
(A) NAME/KEY: Mature peptide
(B) LOCATION: 5..256
(C) IDENTIFICATION METHOD:E
(A) NAME/KEY: MUTATION
(B) LOCATION: 11, 12, 13, 16, 19, 23, 25, 37, 40, 47, 55, 62,
64, 86, 113, 115, 118, 121, 124, 125, 127, 133, 134,
136, 151, 154, 157, 160, 181, 200, 201, 202, 205, 207,
220, 223, 259, 261, 263
(C) IDENTIFICATION METHOD:S (x i) SEQUENCE DESCRIPTION: SEQ ID NO:3:

| | | | | | |
|---|---|---|---|---|---|
| TATGTCTGTG | TCCGAGATTC | AGTTAATGCA | TAACCTTGGC | AAACATTTGA | ACTCCATGGA | 60
| GCGTGTAGAA | TGGCTGCGTA | AGAAGTTGCA | GGATGTGCAC | AATTTTGTTG | CCTTAGGTGC | 120
| CCCATTGGCT | CCTCGTGATG | CTGGTTCCCA | AAGACCACGT | AAAAAGGAAG | ACAATGTCTT | 180
| AGTTGAGAGC | CATGAAAAAT | CCCTAGGCGA | GGCAGACAAG | GCCGATGTGA | ATGTATTAAC | 240
| TAAAGCTAAA | TCCCAGTAAT | GAG | | | | 263

(2) INFORMATION FOR SEQ ID NO:4:

(i) SEQUENCE CHARACTERISTICS:
(A) LENGTH: 265 base pairs
(B) TYPE: nucleic acid
(C) STRANDEDNESS: double
(D) TOPOLOGY: linear (ii) MOLECULE TYPE: DNA (iv) ANTI-SENSE: YES (x i) SEQUENCE DESCRIPTION: SEQ ID NO:4:

| | | | | | |
|---|---|---|---|---|---|
| GATCCTCATT | ACTGGGATTT | AGCTTTAGTT | AATACATTCA | CATCGGCCTT | GTCTGCCTCG | 60
| CCTAGGGATT | TTTCATGGCT | CTCAACTAAG | ACATTGTCTT | CCTTTTTACG | TGGTCTTTGG | 120
| GAACCAGCAT | CACGAGGAGC | CAATGGGGCA | CCTAAGGCAA | CAAAATTGTG | CACATCCTGC | 180
| AACTTCTTAC | GCAGCCATTC | TACACGCTCC | ATGGAGTTCA | AATGTTTGCC | AAGGTTATGC | 240
| ATTAACTGAA | TCTCGGACAC | AGACA | | | | 265

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid, synthesizing DNA (ix) FEATURE:
(A) NAME/KEY: CDS
(B) LOCATION: 2..30
(C) IDENTIFICATION METHOD:E (x i) SEQUENCE DESCRIPTION: SEQ ID NO:5:

TATGTCTGTG  TCCGAGATTC  AGTTAATGCA                    30

(2) INFORMATION FOR SEQ ID NO:6:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: other nucleic acid, synthesizing DNA -continued ( i v ) ANTI-SENSE: YES ( i x ) FEATURE:
    ( A ) NAME/KEY: CDS
    ( B ) LOCATION: 1..34
    ( C ) IDENTIFICATION METHOD:E ( x i ) SEQUENCE DESCRIPTION: SEQ ID NO:6:

AGGTTATGCA TTAACTCAAT CTCGGACACA GACA    34

( 2 ) INFORMATION FOR SEQ ID NO:7:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: other nucleic acid, synthesizing DNA ( i x ) FEATURE:
    ( A ) NAME/KEY: CDS
    ( B ) LOCATION: 1..45
    ( C ) IDENTIFICATION METHOD:E ( x i ) SEQUENCE DESCRIPTION: SEQ ID NO:7:

TAACCTTGGC AAACATTTGA ACTCCATGGA GCGTGTAGAA TGGCT    45

( 2 ) INFORMATION FOR SEQ ID NO:8:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: other nucleic acid, synthesizing DNA ( i x ) FEATURE:
    ( A ) NAME/KEY: CDS
    ( B ) LOCATION: 1..45
    ( C ) IDENTIFICATION METHOD:E ( x i ) SEQUENCE DESCRIPTION: SEQ ID NO:8:

TTACGCAGCC ATTCTACACG CTCCATGGAG TTCAAATGTT TGCCA    45

( 2 ) INFORMATION FOR SEQ ID NO:9:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid, synthesizing DNA ( i x ) FEATURE:
    ( A ) NAME/KEY: CDS
    ( B ) LOCATION: 1..30
    ( C ) IDENTIFICATION METHOD:E ( x i ) SEQUENCE DESCRIPTION: SEQ ID NO:9:

GCGTAAGAAG TTGCAGGATG TGCACAATTT    30

( 2 ) INFORMATION FOR SEQ ID NO:10:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear -continued (ii) MOLECULE TYPE: other nucleic acid, synthesizing DNA (iv) ANTI-SENSE: YES (ix) FEATURE:
    (A) NAME/KEY: CDS
    (B) LOCATION: 1..30
    (C) IDENTIFICATION METHOD:E (xi) SEQUENCE DESCRIPTION: SEQ ID NO:10:

GCAACAAAAT TGTGCACATC CTGCAACTTC     30

(2) INFORMATION FOR SEQ ID NO:11:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: other nucleic acid, synthesizing DNA (ix) FEATURE:
    (A) NAME/KEY: CDS
    (B) LOCATION: 1..46
    (C) IDENTIFICATION METHOD:E (xi) SEQUENCE DESCRIPTION: SEQ ID NO:11:

TGTTGCCTTA GGTGCCCCAT TGGCTCCTCG TGATGCTGGT TCCCAA     46

(2) INFORMATION FOR SEQ ID NO:12:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: other nucleic acid, synthesizing DNA (iv) ANTI-SENSE: YES (ix) FEATURE:
    (A) NAME/KEY: CDS
    (B) LOCATION: 1..46
    (C) IDENTIFICATION METHOD:E (xi) SEQUENCE DESCRIPTION: SEQ ID NO:12:

TGGTCTTTGG GAACCAGCAT CACGAGGAGC CAATGGGGCA CCTAAG     46

(2) INFORMATION FOR SEQ ID NO:13:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: other nucleic acid, synthesizing DNA (ix) FEATURE:
    (A) NAME/KEY: CDS
    (B) LOCATION: 1..41
    (C) IDENTIFICATION METHOD:E (xi) SEQUENCE DESCRIPTION: SEQ ID NO:13:

AGACCACGTA AAAAGGAAGA CAATGTCTTA GTTGAGAGCC A     41

(2) INFORMATION FOR SEQ ID NO:14:

(i) SEQUENCE CHARACTERISTICS:
    (A) LENGTH: 41 base pairs (B) TYPE: nucleic acid
                (C) STRANDEDNESS: single
                (D) TOPOLOGY: linear (ii) MOLECULE TYPE: other nucleic acid, synthesizing DNA (iv) ANTI-SENSE: YES (ix) FEATURE:
                (A) NAME/KEY: CDS
                (B) LOCATION: 1..41
                (C) IDENTIFICATION METHOD:E (xi) SEQUENCE DESCRIPTION: SEQ ID NO:14:

TTTTCATGGC TCTCAACTAA GACATTGTCT TCCTTTTTAC G                41

(2) INFORMATION FOR SEQ ID NO:15:

(i) SEQUENCE CHARACTERISTICS:
                (A) LENGTH: 42 base pairs
                (B) TYPE: nucleic acid
                (C) STRANDEDNESS: single
                (D) TOPOLOGY: linear (ii) MOLECULE TYPE: other nucleic acid, synthesizing DNA (ix) FEATURE:
                (A) NAME/KEY: CDS
                (B) LOCATION: 1..42
                (C) IDENTIFICATION METHOD:E (xi) SEQUENCE DESCRIPTION: SEQ ID NO:15:

TGAAAAATCC CTAGGCGAGG CAGACAAGGC CGATGTGAAT GT               42

(2) INFORMATION FOR SEQ ID NO:16:

(i) SEQUENCE CHARACTERISTICS:
                (A) LENGTH: 42 base pairs
                (B) TYPE: nucleic acid
                (C) STRANDEDNESS: single
                (D) TOPOLOGY: linear (ii) MOLECULE TYPE: other nucleic acid, synthesizing DNA (iv) ANTI-SENSE: YES (ix) FEATURE:
                (A) NAME/KEY: CDS
                (B) LOCATION: 1..42
                (C) IDENTIFICATION METHOD:E (xi) SEQUENCE DESCRIPTION: SEQ ID NO:16:

GTTAATACAT TCACATCGGC CTTGTCTGCC TCGCCTAGGC AT               42

(2) INFORMATION FOR SEQ ID NO:17:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: other nucleic acid, synthesizing DNA (ix) FEATURE:
                (A) NAME/KEY: CDS
                (B) LOCATION: 1..28
                (C) IDENTIFICATION METHOD:E (xi) SEQUENCE DESCRIPTION: SEQ ID NO:17:

ATTAACTAAA GCTAAATCCC AGTAATGAG                              29

-continued ( 2 ) INFORMATION FOR SEQ ID NO:18:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: other nucleic acid, synthesizing DNA ( i v ) ANTI-SENSE: YES ( i x ) FEATURE:
      ( A ) NAME/KEY: CDS
      ( B ) LOCATION: 6..27
      ( C ) IDENTIFICATION METHOD:E ( x i ) SEQUENCE DESCRIPTION: SEQ ID NO:18:

GATCCTCATT ACTGGGATTT AGCTTTA    27

SYNTHETIC GENE CODING FOR HUMAN PARATHYROID HORMONE

This is a continuation of Ser. No. 08/006,197 filed on Jan. 19, 1993, now abandoned, which is a continuation of Ser. No. 07/765,371 filed on Sep. 25, 1991, now abandoned.

BACKGROUND OF THE INVENTION

The present invention relates to a recombinant DNA technique for producing human parathyroid hormone (hereinafter referred to as hPTH), and more specifically to a synthetic gene corresponding to the amino acid sequence of hPTH, DNA containing it, a host cell transformed by the DNA, and a method for producing hPTH using the transformant.

hPTH is a polypeptide hormone secreted from the parathyroid consisting of 84 amino acids, and one of the most important regulators for calcium metabolism. The clinical application of hPTH to various bone diseases such as hypoparathyroidism and osteoporosis has therefore been strongly desired. However, natural hPTH exists in very small amounts and it is also a protein having a relatively low molecular weight. For this reason, though hPTH can be chemically synthesized, the synthesis thereof requires utilizing techniques which require a high level of skill and which are difficult. Accordingly, the production of hPTH using recombinant DNA techniques is desirable.

The DNA sequence of hPTH was first revealed by G. N. Hendy et al. Proc. Natl. Acad. Sci. U.S.A. 78, 7365–7369 (1981). Then, two or three groups attempted to synthesize hPTH using microorganisms to clone cDNA of hPTH and insert it into various expression vectors. Alestrφm et al. attempted to express and secrete cDNA-derived genes in yeast (Japanese Patent Unexamined Publication No. 2-501108/1990). However, they did not succeed in isolating and identifying hPTH. A. Høgset et al. prepared a gene containing a Met-Gly residue at the N-terminus of hPTH from an hPTH cDNA clone, and expressed the gene in *Escherichia coli* Blochem. Biophys. Res. Commun. 166, 50–60 (1990). However, the resulting hPTH protein had a Met-Gly residue added to the N-terminus thereof and did not exhibit the activity of hPTH. E. Wingender et al. expressed hPTH in *E. coli* as a fused protein with β-galactosidase *J. Biol. Chem.* 246, 4367–4373 (1989). However, this protein whose unnecessary portions were removed was a molecule having Pro added to the N-terminus. A. Høgset et al. succeeded in ligating cDNA of hPTH downstream from a *Staphylococcus aureus*-protein A promoter and a signal peptide gene, expressing and secreting it outside the cells by *E. coli*, as well as isolating and identifying hPTH *J. Biol. Chem.* 265, 7338–7344 (1990). However, the yield is only about 1 mg/liter of culture solution, and the expression amount is insufficient from an industrial viewpoint, particularly when the loss of the product during the purification process is taken into account.

When a gene encoding a protein of a certain living organism is intended to be expressed in other hosts, the method of synthesizing that gene chemically is also used as a method for obtaining the gene, in addition to the method of using the gene derived from the living organism. In recent years, automatic synthesis techniques of DNA oligomers have been developed. When the molecular weight of the protein is relatively low and the amino acid sequence or DNA sequence thereof is known, the method of synthesizing the gene is frequently more advantageous for the following reasons:

(1) The desired gene is relatively easily obtained;

(2) A terminal sequence used when inserting the gene into a plasmid or a recognition sequence of a restriction enzyme appropriate for modification of the gene can be freely introduced; and (3) A gene sequence can be designed so that the desired gene product is highly expressed.

W. L. Sung et al. synthesized a structural gene encoding hPTH, using an amino acid codon most acceptable by yeast *Biochem. Cell. Biol.* 64, 133–138 (1986). Also S. A. Rabbani et al. expressed this gene in *E. coli, J. Biol. Chem.* 263, 1307–1313 (1988), however, its yield of about 200 μg/l was very low and thus not practical.

As described above, attempts have been made to express hPTH in various systems using the cDNA-derived or synthetic genes. In either case, however, the yield was very low and insufficient from an industrial viewpoint.

SUMMARY OF THE INVENTION

The present invention provides an amino acid sequence of hPTH, appropriate for solving the above-described problems, as well as a method for producing the gene, recombinant DNA containing the gene, a host cell transformed by the DNA and a method for producing hPTH using the transformant.

In accordance with the present invention, there is provided (1) DNA containing a synthetic gene for expression of human parathyroid hormone represented by the following DNA sequence (SEQ ID NO: 1):

TCTGTG TCCGAGATTC AGTTAATGCA TAACCT-
TGGC AAACATTTGA ACTCCATGGA GCGTGTAGAA
TGGCTGCGTA AGAAGTTGCA GGATGTGCAC
AATTTTGTTG CCTTAGGTGC CCCATTGGCT
CCTCGTGATG CTGGTTCCCA AAGACCACGT
AAAAAGGAAG ACAATGTCTT AGTTGAGAGC CAT-
GAAAAAT CCCTAGGCGA GGCAGACAAG GCCGAT-
GTGA ATGTATTAAC TAAAGCTAAA TCCCAG (2) a method for producing the DNA described in (1), which comprises enzymatically ligating a plurality of oligodeoxynucleotides, one to another, to form the DNA and inserting the DNA into a vector if necessary, (3) a host cell transformed by the DNA described in (1), and (4) a method for producing human parathyroid hormone which comprises cultivating the transformant described in (3), accumulating human parathyroid hormone in a culture medium, and collecting the same.

BRIEF DESCRIPTION OF THE DRAWINGS

FIG. 1 shows an amino acid sequence and a nucleotide sequence of the synthetic gene of the present invention encoding hPTH;

FIG. 2 is a schematic representation showing an example of cleavage of DNA fragments in synthesizing the hPTH gene of the present invention;

FIG. 3 is a schematic representation showing an example of DNA fragments for producing synthetic genes of the present invention encoding hPTH;

FIG. 4-1 is a schematic representation illustrating the production of a synthetic hPTH gene by ligating the respective fragments shown in FIG. 3 one to another;

FIG. 4-2 is a schematic representation illustrating the production of a synthetic hPTH gene by ligating the respective fragments shown in FIG. 3 one to another;

FIG. 9 shows electrophoresis and Western blot results of an hPTH sample, in which lane 1 shows a prestained molecular weight marker, lane 2 shows purified hPTH obtained by the present invention, and lane 3 shows a standard hPTH sample;

FIG. 10 shows an electrophoresis and Western blot results for an hPTH sample, in which lane 1 shows a prestained molecular weight marker, lane 2 shows purified hPTH obtained by the present invention, and lane 3 shows a standard hPTH sample; and FIG. 11 is a graph showing the biological activity of hPTH fragments, in which -*- shows a synthetic hPTH(1-34) fragment, and - - - shows purified hPTH obtained by the present invention.

DESCRIPTION OF THE PREFERRED EMBODIMENTS

Figures 1, 4:
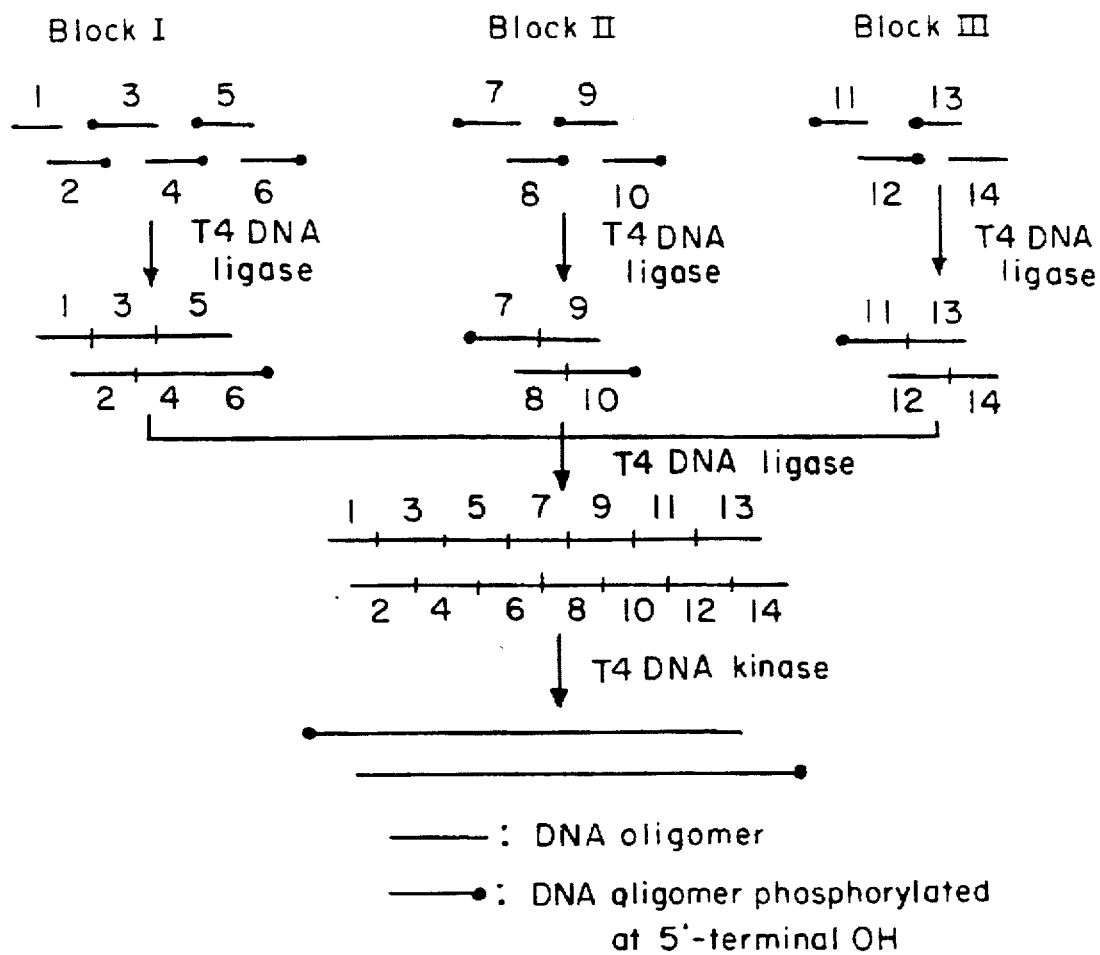

Sequences of synthetic genes are designed so as to satisfy various conditions to enhance the expression of the genes. One of the conditions is that codons most acceptable by cells of expression systems should be employed. Accordingly, in the hPTH genes of the present invention, codons are employed which are frequently used for the production of proteins by recombinant technology and accepted by both *E. coli* and yeast. Further, consideration is given to arranging recognition sequences of restriction enzymes convenient for modification of the genes at appropriate positions when selecting the codons. Furthermore, to construct the desired genes accurately, relatively long, unnecessary palindrome sequences and directly repeated sequences existing on DNA chains are removed as much as possible. As additional conditions to enhance the expression of the genes, the stability and translation efficiency of mRNAs corresponding to structural genes should be considered. In this case, secondary structure determined by nucleotide sequences of mRNAs is believed to be of importance. Therefore, for the hPTH genes of the present invention, hairpin structures and the like are searched for using a computer during the course of design, and the sequence is then modified, preferably by removing it. Thus, a novel DNA sequence most suitable for the production of hPTH as shown in FIG. 1 (SEQ ID NO:1) has been discovered. This gene sequence is about 25.4% different from the above-described gene of W. L. Sung et al. in DNA sequence. In addition to the DNA sequence, the amino acid sequence is shown in FIG. 1.

The gene can be expressed as either a fused peptide or hPTH directly without forming the fused peptide.

In the former case, either a DNA sequence starting with an initiation codon ATG and coding for a protein other than hPTH may be arranged at the 5'-terminal side of the synthetic gene of hPTH, and it ends in a stop codon (for example, TAA); or a DNA sequence coding for a protein other than hPTH may arranged at the 3'-terminal side of the synthetic gene of hPTH starting with an initiation codon ATG and it ends in a stop codon (for example, TAA).

Figures 2, 4:
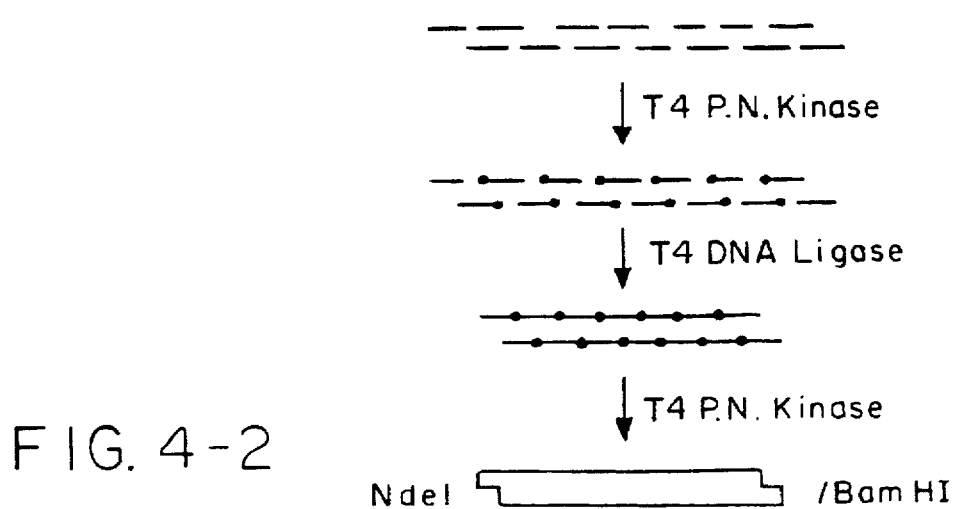

In the case of direct expression, the initiation codon ATG and a stop codon (for example, TAA) are directly arranged on the 5'- and 3'-terminal sides, respectively, and the 5'- and 3'-termini have, for example, NdeI and BamHI cohesive ends, respectively, for insertion into a vector, in addition to a sequence coding for a polypeptide of hPTH, as shown in FIG. 2 (SEQ ID NO:2).

In synthesizing the hPTH gene of the present invention, the hPTH gene is finally cleaved into 14 fragments, for example, as shown in FIG. 2 (SEQ ID NO:2, SEQ ID NO:3). In this case, care is taken so as to avoid self-linkage between fragments, e.g. a self-complimentary sequence at the 5'- or 3'-terminus. The respective fragments are shown in FIG. 3. Methods for cleaving the gene into the fragments are not limited to the above-mentioned method, and various methods are available as long as the above self-linkage is avoided.

Fragments #1 to #14 (SEQ ID NOS: 4 to 17) can be produced by known synthesizing methods. For the fragments, except for #1 and #14, the termini are phosphorylated at 5'-termini with polynucleotide kinase as so required, and all of the fragments are hybridized to ligate them to one another with DNA ligase, or the phosphorylated fragments first divided into two or three groups are hybridized to form a double stranded DNA fragment with DNA ligase, and the DNA fragments of the respective groups are further ligated to one another with DNA ligase, thereby obtaining a complete double stranded hPTH gene (refer to FIG. 4).

The resulting gene is ligated to a product obtained by digesting pUC19 with NdeI and BamHI to obtain a novel plasmid pU.PTH.C19, and *E. coli* JM109 is transformed. As to the isolated plasmid, the nucleotide sequence is determined by the Sanger method using a portion of the DNA fragment as a primer. More easily, the DNA fragment obtained by NdeI-BamHI digestion is digested with AvrII, NcoI, HgiAI or AluI to give a correct restriction site, thereby confirming the existence of the desired hPTH gene.

When the synthetic gene of the present invention is expressed, it is preferably used as a recombinant DNA inserted into vectors such as plasmids or bacteriophages.

Examples of such plasmids include pBR322 [Gene 2, 95 (1977)], pBR325 [Gene 4, 121 (1978)], pUC12 [Gene 19, 259 (1982)] and pUC13 [Gene 19, 259 (1982)], each derived from *Escherichia coli*, and pUB110 derived from *Bacillus subtilis* [*Biochemical and Biophysical Research Communication* 112, 678 (1983)]. However, any other plasmids can be used as long as they are viable in the host cells. Examples of the phage vectors include λgt11, R. Young and R. Davis, *Proc. Natl. Acad. Sci. U.S.A.* 80, 1194 (1983). However, any other phage vectors can be used as long as they are viable in the host cells.

The plasmids thus obtained are introduced into appropriate host cells such as Escherichia, Bacillus, yeast and animal cells.

Methods for transforming the host cells with the plasmids include, for example, the calcium chloride method or the calcium chloride/rubidium chloride method described in T.

Maniatis et al., *Molecular Cloning*, Cold Spring Harbor Laboratory, p.249 (1982).

When phage vectors are used, for example, they can be transduced into proliferated *E. coli*, using the in vitro packaging method.

It is preferred that the above-mentioned recombinant DNA has a promoter upstream from the above-mentioned initiation codon ATG, and as the promoter, any promoter may be employed as long as it is suitable for the host cells used for the production of transformants.

For example, a trp promoter, a lac promoter, a recA promoter, a λPL promoter, a lpp promoter, T7 promoter, etc. may be used for *E. coli* (for example, MM294, BL21, BL21/PLys, W3110, DH1 and N4830); a SP01 promoter, a SP02 promoter, a penP promoter, etc. may be used for *Bacillus subtilis* (for example, MI114); a promoter for major cell wall proteins, etc. may be used for *Bacillus brevis;* a PHO5 promoter, a PGK promoter, a GAP promoter, an ADH promoter, etc. may be used for *Saccharomyces cerevisiae* (for example, AH22); and an SV40-derived promoter, mouse leukemia virus (MuLV)-derived LTR region promoter, etc. may be used for animal cells (for example, monkey cell COS-7 and Chinese hamster ovary cell (CHO)). In particular, it is preferred that the promoter is the T7 promoter, the trp promoter or the λPL promoter when the host cell is *E. coli*, and that an enhancer is used in addition to the above-mentioned promoter when the host cell is an animal cell.

The transformants thus obtained are cultivated in the known media. The media for the transformants of *Escherichia coli* include, for example, LB medium.

The transformants of *Escherichia coli* are cultivated usually at 15° to 43° C. for 2 to 24 hours, preferably at 28° to 40° C. for 4 to 16 hours, with aeration or agitation if necessary. After cultivation, the cells are collected by methods known in the art. In the case of the transformants of *Escherichia coli*, the cells are suspended in buffer solutions or buffer solutions containing protein denaturants such as urea and guanidine hydrochloride, and disrupted by mechanical disruption such as ultrasonic treatment, lysozyme treatment and glass bead treatment, followed by centrifugation to obtain extracted solutions containing hPTH. hPTH can be separated and purified from the extracted solutions by known means. The separating and purifying means include column chromatography such as gel filtration, ion exchange chromatography using a cation exchange resin or an anion exchange resin, hydrophobic chromatography and partition adsorption chromatography, and high performance liquid chromatography. The cultivation of the transformants of the Bacillus, the yeast and the animal cells and the separation and purification of hPTH from the cultures are carried out by methods known in the art.

hPTH thus obtained can be used as a therapeutic agent for various diseases caused by an abnormality of the calcium metabolism, for example, osteoporosis, hypoparathyroidism and hypertension. The dosage thereof is properly determined, taking into account the object of administration, the disease, etc. in each case, and a suitable amount is given within the range of 1 ng to 100 μg/kg of weight a day. Usually, hPTH is given parenterally in combination with pharmaceutically acceptable carriers, excipients or diluents as injections, nasotracheal agents, perrectum agents, transvaginal agents or percutaneous agents, but it may be given orally in some cases.

One example of the expression of the hPTH gene is described below (refer to FIG. 5).

A DNA fragment of 267 base pairs cut out of pU.PTH.C19 with NdeI-BamHI was inserted into a NdeI-BamHI site to obtain a vector pET. PTH. 3C for expression under T7 promoter control.

Figure 6:
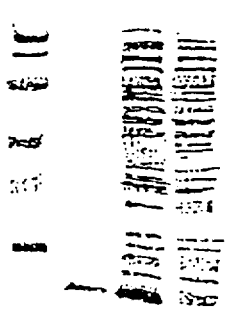
FIG. 6 shows electrophoresis and Western blotting blot results indicating the production of hPTH in a transformant by a gene of the present invention, in which lane 1 shows a molecular weight marker, lane 2 shows a standard sample of hPTH, lane 3 shows an extract (corresponding to 10 μl of culture solution) of a transformant induced by isopropyl-β-D-thiogalactopyranoside (IPTG), and lane 4 shows an extract (corresponding to 10 μl of culture solution) of a transformant not induced by IPTG.
Figure 7:
FIG. 7 shows electrophoresis and Western blot results indicating the production of hPTH in a transformant by a gene of the present invention, in which lane 1 shows a prestained molecular weight marker, lane 2 shows an extract (corresponding to 10 μl of culture solution) of a transformant not induced by IPTG, lane 3 shows an extract (corresponding to 10 μl of culture solution) of a transformant induced by IPTG, and lane 4 shows a standard PTH sample.

*E. coli* BL21 was transformed using pET.PTH.3C, and growing colonies were selected based upon ampicillin resistance to obtain a strain containing a desired hPTH gene. This transformant strain was cultivated, and cells were collected by centrifugation. hPTH contained in a solution treated with 7M guanidine was stained with Coomassie Brilliant Blue (CBB) after SDS-polyacrylamide electrophoresis (SDS-PAGE), or immunoblotting was conducted by an hPTH antibody after SDS-PAGE, thereby determining hPTH. As a result, the product was produced in amounts of about 200 mg/l or more (refer to FIGS. 6 and 7). This expression amount is vastly increased as compared to prior attempts of as the direct expression of hPTH in *E. coli*.

In the present invention, the codon most acceptable in cells of expression systems is employed as the DNA sequence of the hPTH gene, and the gene is designed, also taking into account the secondary structure of mRNA corresponding to the DNA sequence, whereby the translation efficiency of mRNA are improved, which results in the efficient production of hPTH. Further, in the present invention, the arrangement of the recognition sites of several kinds of restriction enzymes in the structural gene makes the insertion of the gene and the confirmation of an inserting direction easy, and makes the modification of the gene easy to produce analog proteins of hPTH. Moreover, the gene can be inserted into several kinds of vectors. Thus, the advantage and the diversity on gene manipulation can be exhibited.

EXAMPLE 1

1. Synthesis of DNA Fragments

Fourteen DNA fragments #1 to #14 (SEQ ID NO: Nos. 4 to 17) shown in FIG. 3 were synthesized using properly protected DNA β-cyanoethylphosphoamidite, and using an automatic synthesizer (Model 380A, Applied Biosystems). As a protocol for synthesis, the one specified by Applied Biosystems was used. The protected DNA oligomer-resins thus synthesized (0.2 μmole of the resin) were heated in 2 ml of concentrated aqueous ammonia at 60° C. for 6 hours. The resulting products were purified by reversed phase high performance liquid chromatography (hereinafter referred to as HPLC) to obtain DNA oligomers only the 5'-terminal hydroxyl groups of which were protected by dimethoxytrityl groups. These DNA oligomers were treated with 2 ml of 80% acetic acid for 20 minutes to remove the terminal dimethoxytrityl groups, and the resulting products were purified by reversed phase HPLC and ion exchange HPLC. The fourteen DNA oligomers thus synthesized are as shown in FIG. 3 (SEQ. NOS: 4 to 17).

2. Phosphorylation of DNA Oligomers

Each of the twelve DNA oligomers #2 to #13 (SEQ ID NOS: 5 to 16) except for #1 (SEQ ID NO: 4) and #14 (SEQ ID NO: 17) which were to form the 5'-termini was reacted in 25 μl of a phosphorylation reaction solution [10 μl of the DNA oligomer, 50 mM Tris-HCl (pH 7.6), 10 mM $MgCl_2$, 1 mM spermidine, 10 mM dithiothreitol (hereinafter referred to as DTT), 0.1 mg/ml bovine serum albumin (hereinafter referred to as BSA), 1 mM ATP, 10 units of T4 polynucleotide kinase (Takara Shuzo)] at 37° C. for 1 hour to phosphorylate the 5'-terminus. This reaction solution was treated at 65° C. for 10 minutes, followed by freezing and thawing. The resulting product was subjected to the following reaction.

3. Ligation of DNA Fragments (Refer to FIGS. 4-1 and 4-2)

3-1 A series of stages for forming a double stranded structure of an hPTH gene are as shown in FIG. 4-1.

Referring to FIG. 4-1, the mark — indicates that a 5'-terminal hydroxyl group is phosphorylated. For example, the ligation of block I was carried out as follows. 7.5 μl portions of the phosphorylated reaction solutions of the five DNA fragments [corresponding to DNA fragments #2 to #6 (SEQ ID NOS: 5 to 9)] obtained by the operation described in the above item 2 were combined with 2.5 μg of DNA fragment #1 (SEQ NO: 4) corresponding to the 5'-terminus to 50 μl. Then, 5 units of T4 DNA ligase (New England Biolabs) was added thereto, followed by incubation at 14° C. for 5 hours. The resulting product was thereafter treated at 65° C. for 10 minutes to terminate the reaction, thus obtaining block I. Blocks II and III were similarly prepared. 20 μl portions of these block I to III were mixed and 5 units of T4 DNA ligase was added thereto, followed by incubation at 14° C. for 20 hours. The resulting product was treated at 65° C. for 10 minutes to terminate the reaction.

The product thus obtained was subjected to electrophoresis on a 7.5% polyacrylamide gel in a buffer (pH 8.3, 100 mM Tris-HCl, 100 mM borate, 2 mM EDTA) at 160 V for 1.5 hours. After electrophoresis, the gel was stained with 0.6 mg/l ethidiumbromide (EtBr). Gel fragments containing 263-bp DNA fragments were sealed in a dialysis tube and submerged in a buffer for electrophoresis. Then, the DNA fragments were electrically eluted from the gel [*J. Mol. Biol.* 110, 119 (1977)]. A solution in this dialysis tube was recovered and poured on an Elutip-d column (Schleicher & Schnell) previously buffered with a solution containing 0.2M NaCl, 20 mM Tris-HCl (pH 7.4) and 1.0 mM EDTA to allow the DNA fragment to be adsorbed. Then, the DNA fragments were eluted with a solution containing 1.0M NaCl, 20 mM Tris-HCl (pH 7.4) and 1.0 mM EDTA. Twice as much ethanol as the eluate was added to the eluate, and the mixture was cooled to −20° C. Then, the DNA fragments were precipitated by centrifugation.

3-2 A series of stages for forming a double stranded structure of an hPTH gene can also be achieved by a process shown in FIG. 4-2. Referring to FIG. 4-2, the mark — indicates that a 5'-terminal hydroxyl group is phosphorylated. 5 μl portions of the phosphorylated reaction solutions of the twelve kinds of DNA fragments [corresponding to DNA fragments #2 to #13 (SEQ NOS: 5 to 16)] obtained in the above item 2 were combined with 2 μg of DNA fragments #1 (SEQ ID NO: 4) and #14 (SEQ ID NO: 17) corresponding to the 5'-terminus to 50 μl. Then, 5 units of T4 DNA ligase (Takara Shuzo) was added thereto, followed by incubation at 15° C. for 20 hours.

The product thus obtained was subjected to electrophoresis on a 8% polyacrylamide gel in a buffer (pH 8.3, 100 mM Tris-HCl, 100 mM boric acid, 2 mM EDTA) at 125 V for 2 hours. After electrophoresis, the gel was stained with 0.6 mg/l EtBr. Gel fragments containing 263-bp DNA fragments were sealed in a dialysis tube and submerged in a buffer for electrophoresis. Then, the DNA fragments were electrically eluted from the gel. A solution in this dialysis tube was subjected to phenol treatment twice, followed by recovery of an aqueous layer (an upper layer). Then, twice as much ethanol as the aqueous layer was added thereto, and the mixture was cooled to −70° C. The DNA fragments were thereafter precipitated by centrifugation. Thus, about 1 μg of the DNA fragments was obtained. After phosphorylation with T4 polynucleotide kinase (Takara Shuzo), the DNA fragments were subjected to the following experiment 4-2.

4. Cloning of hPTH Gene (FIG. 5)

4-1 As a cloning vector, *E. coli* plasmid pBR322-derived pUC19 [J. Messing, *Gene* 33 103–109 (1985)] was used. pUC19 DNA was reacted in 20 μl of a reaction solution [20 mM Tris-HCl (pH 7.6), 7 mM MgCl$_2$, 150 mM NaCl, 10 mM 2-mercaptoethanol, 20 units of NdeI (New England Biolabs), 15 units of BamHI (Takara Shuzo)] at 37° C. for 24 hours. Then, the resulting product was diluted 5 times with water, and treated at 65° C. for 20 minutes to inactivate the enzyme. 5 μl of this reaction solution was mixed with about 5 equivalents of the DNA fragments obtained in the above item 3-1 to prepare 20 μl of a reaction solution containing 50 mM Tris-HCl (pH 7.5), 10 mM MgCl$_2$, 10 mM DTT, 1 mM spermidine, 0.1 mg/ml BSA and 1 mM ATP. Then, T4 DNA ligase (New England Biolabs) was reacted with this solution at 14° C. for 15 hours to ligate the hPTH gene to the plasmid.

Using this reaction solution, the *E. coli* JM109 strain [J. Messing, *Gene* 33, 103–119 (1985)] was transformed according to methods known in the art. Namely, 50 μl of competent cells [D. Hanahan, *J. Mol. Biol.* 166, 557 (1983)] stored at −70° C. was incubated at 0° C. for 15 minutes, and then 10 μl of the above-mentioned reaction solution was added thereto. The resulting solution was further incubated at 0° C. for 15 minutes, and then incubated at 42° C. for 1.5 minutes and further at 0° C. for 2 minutes. To this reaction solution was added 200 μl of LB medium (containing 10 g of Bacto-tryptone, 5 g of a Bacto-yeast extract and 5 g of NaCl), and incubated at 37° C. for 1 hour. This *E. coli* was seeded onto LB agar medium containing 50 μg/ml ampicillin, 100 μg/ml X-Gal and 0.1 mM isopropyl-β-D-thiogalactopyranoside (IPTG), and incubated at 37° C. overnight. Of the resulting ampicillin-resistant colonies, 14 β-galactosidase-deficient strains were selected and plasmid DNAs of transformed strains thereof were crudely purified by the alkali method [T. Maniatis et al., *Molecular Cloning*, (Cold Spring Harbor Laboratory) 368–369 (1982)], followed by digestion with NcoI and BamHI, and further with NdeI and BamHI. The electrophoresis patterns of these digests on a 1.7% agarose gel revealed that one strain was a transformed strain into which the hPTH gene was correctly inserted.

4-2 The hPTH gene was also cloned by the following method. As a cloning vector, pUC19 (Takara Shuzo) was used. 0.5 μg of pUC19 DNA was reacted in 10 μl of a reaction solution [50 mM Tris-HCl (pH 7.5), 10 mM MgCl$_2$, 100 mM NaCl, 1 mM dithiothreitol, 20 units of NdeI (New England Biolabs), 10 units of BamHI (Takara Shuzo)] at 37° C. for 5 hours. Then, the resulting product was treated at 65° C. for 15 minutes to inactivate the enzyme. 1 μl of this reaction solution was mixed with about 10 equivalents of the DNA fragment obtained in the above item 3-2, and the hPTH gene was ligated to the plasmid using a DNA ligation kit (Takara Shuzo). The transformation into the *E. coli* JM109 strain was carried out in the same manner as with the above item 4-1. Of the resulting ampicillin-resistant colonies, 17 β-galactosidase-deficient strains were selected and plasmid DNAs of transformed strains thereof were crudely purified by the alkali method, followed by digestion with NcoI and BamHI, and further with NdeI and BamHI. The electrophoresis patterns of these digests on a 1.5% agarose gel revealed that three strains were transformed strains into which the hPTH gene was correctly inserted.

The cloning vectors obtained in the above items 4-1 and 4-2 were named pU.PTH.C19. 20 ml of LB medium containing 50 μg/ml ampicillin was inoculated with one loopful of *E. coli* JM109 recombinants having this plasmid pU.PTH.C19, and cultivated at 37° C. overnight with shaking. Plasmid DNA was crudely purified from this culture solution, and dissolved in 80 μl of TE buffer [10 mM Tris-HCl (pH 8.0), 1 mM EDTA] containing 20 μg/ml RNase.

EXAMPLE 2

Figure 5:
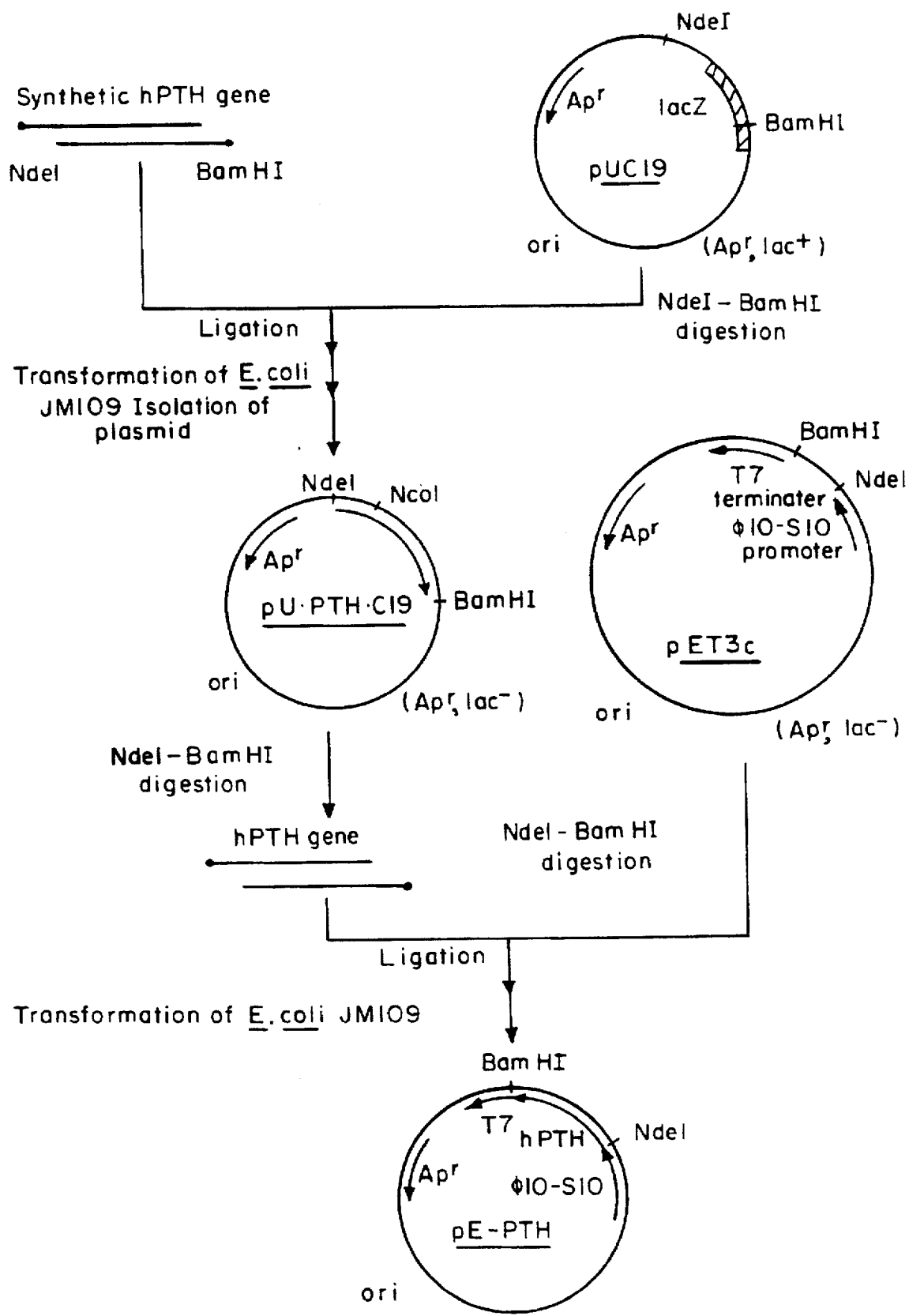
FIG. 5 is a schematic representation showing the construction of a plasmid for expression into which a synthetic gene of the present invention encoding hPTH is inserted.

Construction of Plasmid for Expression of hPTH and Production of Transformant (FIG. 5)

1) About 10 μg of pU.PTH.C19 obtained in the above item 4 of Example 1 was reacted in a reaction solution [150 mM NaCl, 20 mM Tris-HCl (pH 7.8), 7 mM $MgCl_2$, 10 mM mercaptoethanol, 40 units of NdeI, 20 units of BamHI (Takara Shuzo)] at 37° C. for 5 hours. Then, 263-bp DNA fragments were purified by 1.7% agarose gel electrophoresis according to known methods. On the other hand, as a vector for expression, pET3C [F. W. Stadier et al., *Methods in Enzymology* 195, 60–89 (1990)] was used. pET3C DNA was digested with NdeI and BamHI in the same manner as above, and four times as much water as the resulting reaction solution was added thereto, followed by heating at 65° C. for 20 minutes to inactivate the enzymes.

Each of the 263-bp DNA and the plasmid DNA has single stranded cohesive ends produced by NdeI digestion and BamHI digestion at both ends thereof.

Both of them were mixed with each other, and the mixture was reacted with T4 DNA ligase (New England Biolabs) in the presence of 50 mM Tris-HCl (pH 7.6), 10 mM $MgCl_2$, 10 mM DTT, 1 mM spermidine, 0.1 mg/ml BSA and 1 mM ATP at 14° C. for 16 hours to ligate the DNAs to each other, followed by transformation of the *E. coli* JM109 strain in the same manner as above. Then, this *E. coli* was seeded onto LB agar medium containing 50 μg/ml ampicillin, and cultivated at 37° C. for 1 day. The resulting ampicillin-resistant colonies were selected. Plasmid DNAs of the transformed strains were further digested by combinations of restriction enzymes such as NdeI-BamHI, BglII-BamHI, EcoRI-NdeI and AvrII-BglII. Transformed strains containing the correct hPTH genes were selected by their patterns of polyacrylamide electrophoresis. The plasmids for expression thus obtained were named pE-PTH, and the transformed strains were named *E. coli* JM109/pE-PTH.

2) Plasmid DNAs were isolated from JM109/pE-PTH obtained in the above item 1), and crudely purified to transform *E. coli* MM294(DE3) having T7 RNA polymerase necessary for expression of a T7 promoter (European Unexamined Laid-Open patent application No. 416505). First, 10 ml of LD medium was inoculated with one loopful of *E. coli* MM294(DE3), and cultivated at 37° C. with shaking to a Klett of 60 to 180. To this culture solution were added 10% w/v polyethylene glycol, 5% v/v dimethyl sulfoxide and 50 mM $MgCl_2$ (pH 6.5), and a reaction solution was brought up to 100 μl with the addition of LB medium. 10 mg of the plasmid DNAs were added thereto, and incubated at 4° C. for 10 minutes, followed by seeding onto LB agar medium containing 50 μg/ml ampicillin. Then, cultivation was carried out overnight at 37° C.

Plasmid DNAs obtained from the resulting colonies similarly with the method described above were digested with restriction enzymes, and transformed strains containing the hPTH genes were selected by their patterns of electrophoresis. These strains were named *E. coli* MM294(DE3)/pE-PTH.

*E. coli* MM294(DE3) pE-PTH was deposited with the Institute for Fermentation, Osaka, Japan (IFO) under the accession number IFO 15087 on Aug. 28, 1990, and also deposited with the Fermentation Research Institute, the Agency of Industrial Science and Technology, the Ministry of International Trade and Industry, Japan (FRI) under the accession number FERM BP-3110 on Sep. 25, 1990.

EXAMPLE 3

Production of hPTH

1) *E. coli* MM294(DE3) pE-PTH was cultivated overnight at 37° C. in LB medium containing 50 μg/ml ampicillin with shaking. 100 μl of the resulting culture solution was added to 10 ml of the same medium dispensed in 200 ml flasks, and cultivated at 37° C. to a Klett of about 170. Then, IPTG was added thereto to a concentration of 0.1 mM. After cultivation was further continued for 2 hours, 1 ml of the culture solution was centrifuged at 15,000 rpm at 4° C. for 5 minutes. The resulting cells were dissolved in 100 μl of a solution containing 0.5M Tris-HCl (pH 6.8), 10% glycerol, 10% (w/v) sodium dodecyl sulfate (SDS), 0.1% (w/v) β-mercaptoethanol and bromophenol blue [U. K. Laemmli, *Nature* 227, 680 (1970). After boiling for 3 minutes, the solution was subjected to 16% SDS-polyacrylamide gel electrophoresis (PAGE). After electrophoresis, the gel was stained with Coomassie Brilliant Blue. As a result, an intense band indicating the same mobility as that of a standard hPTH sample was observed (refer to FIG. 6). Further, another gel was subjected to western blotting using an hPTH antibody. As a result, the same stain pattern as with the standard hPTH sample was obtained (refer to FIG. 7). Quantitative comparison with the standard sample for the stain of the gels and western blotting revealed that hPTH is expressed in an amount of about 200 mg per liter of culture solution.

2) hPTH accumulated in *E. coli* was purified in the following manner. Cells from 200 ml of a culture solution obtained similarly with the above-mentioned method were suspended in a buffer (5 ml) containing 8M urea, 50 mM Tris-HCl (pH 7.5), 50 mM EDTA and 1 mM α-toluenesulfonyl fluoride, and vigorously stirred under ice cooling for about 1 hour to disrupt the cells, followed by centrifugation at 15,000 rpm at 4° C. for 20 minutes. The supernatant was recovered, and the precipitate was similarly extracted twice with 3 ml portions of a buffer having the same composition. The extracts were combined with the supernatant, followed by two-fold dilution. The resulting solution was passed through a CM-Toyo Pearl column (10 ml) of TSK-Gel (Tosoh) equilibrated with 50 mM ammonium acetate buffer (pH 5) containing 4M urea to allow a desired product to be adsorbed. The column was washed with 50 mM ammonium acetate buffer (pH 5) containing 4M urea. About 10 ml of the buffer was required for washing. When absorption at 280 nm disappeared, the column was developed by a linear gradient of 50 ml of 50 mM ammonium acetate buffer (pH 5)-50 ml of 0.5M ammonium acetate buffer (pH 6) (flow rate: 10 ml/hour, volume of 1 fraction: 2 ml). Fractions 33 to 47 were collected and lyophilized. These fractions were subjected to reversed phase HPLC under the following conditions:

Column: YMC-Pack A-325 S-5 120A ODS (1×30 cm) (Y. M. C.)

Solvent: A linear gradient of 25% to 50% acetonitrile containing 0.1% trifluoroacetic acid (for 30 minutes)

Flow rate: 3 ml/minute

The main peak (retention time: 17.0 minutes) contained the desired product. The resulting eluate was passed through a Bio-Rad AG1X8 (acetate form) column (Bio-Rad Laboratory) and the washings were also combined therewith. Then, acetonitrile was removed by distillation, followed by lyophilization. 4.2 mg of desired hPTH was obtained as a white powder.

Figure 8:
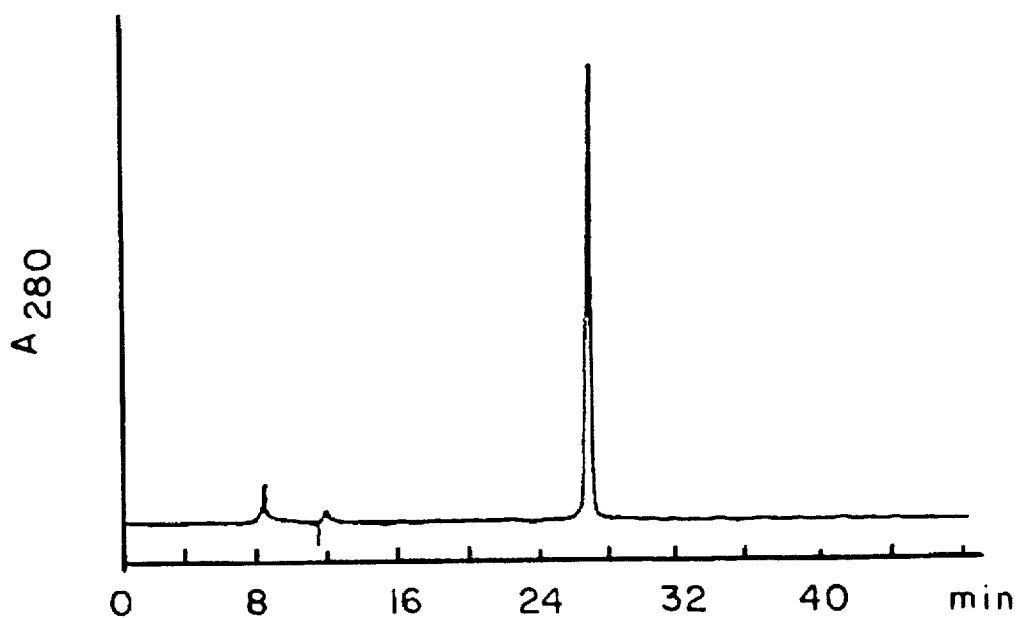
FIG. 8 shows an elution pattern of purified hPTH obtained by reversed phase high performance liquid chromatography.

The following analytical results revealed that this sample was hPTH of high purity.

a) Reversed phase HPLC showed a single sharp peak (refer to FIG. 8).

Column: YMC-Pack A-324 S-5 DDS 120A (10×300 mm)
Eluents: Solution A (0.1% trifluoroacetic acid)
Solution B (acetonitrile containing 0.1% trifluoroacetic acid)
Linear gradient: 0 to 3 minutes (0%, B), 3 to 10 minutes (0 to 30%, B), 10 to 70 minutes (30 to 45%, B)

b) SDS-PAGE and western blotting after electrophoresis also showed a single band of the same mobility as that of the standard sample. The conditions were the same as with FIGS. 6 and 7 (refer to FIGS. 9 and 10).

c) Amino acid analysis (hydrolyzed with 5.7N hydrochloric acid in the presence of thioglycollic acid in a sealed tube under reduced pressure at 110° C. for 24 hours, and values in parentheses indicate theoretical values):

Asp (10) 10.5; Thr (1) 0.96; Ser (7) 6.04; Glu (11) 11.73; Pro (3) 2.88; Gly (4) 4.69; Ala (7) 7.03; Val (8) 7.91; Met (2) 1.96; Ile (1) 1.06; Leu (10) 10.6; Phe (1) 1.10; Lys (9) 9.32; His (4) 4.04; Arg (5) 4.00; Trp (1) 0.97

(Recovery: 82.3%)

d) N-terminal amino acid sequence analysis by a gas-phase sequencer Model 470A (Applied Biosystems) revealed that the sequence from the 1-position Ser to the 15-position Leu was correct.

e) In first atom bombardment mass spectrometry analysis [JMS-HX110 (Nihon Denshi) was used] after cyanogen bromide cleavage in 0.1N hydrochloric acid, the following peaks were observed:

(The 1-position to the 7-position)—homoserine (MH+) Found: 858.5 Theoretical: 858.5

(The 1-position to the 17-position)—homoserine (MH+) Found: 1990.2 Theoretical: 1990.0

(The 9-position to the 17-position)—homoserine (MH+) Found: 1102.7 Theoretical: 1102.7

No peak derived from formylhomoserine or homoserine was observed.

Also in analysis after digestion with asparagine-specific endopeptidase, the following peaks were observed:

(The 1-position to the 16-position) (MH+) Found: 1819.9 Theoretical: 1819.9

(The 17-position to the 33-position) (MH+) Found: 2168.8 Theoretical: 2168.1

(The 58-position to the 76-position) (M+Na) Found: 2061.8 Theoretical: 2062.0

(The 77-position to the 84-position) (MH+) Found: 874.4 Theoretical: 874.5

From the results obtained above, it was judged that hPTH obtained here did not contain Met or formyl-Met at the N-terminus thereof and had a structure starting with the 1-position Ser and ending in the C-terminal 84-position Gln.

Experimental Example

The biological activity of hPTH thus obtained was assayed by a modified method of Shigeno et al.[*The Journal of Biological Chemistry* 263. 18369–18377 (1988)]. A culture solution (Hank's solution containing 20 mMN-2-hydroxyethylpiperazine-N'-2-ethanesulfonic acid (HEPES), 0.1% bovine serum albumin and 0.5 mM isobutylmethylxanthine) containing 0.01, 0.1, 1, 10 or 100 nM the present analogue was added in an amount of 100 µl to a mouse cranial bone-derived osteoblast-like cell strain, MC3T3-EI cells, cultivated on a 96-well multiplate (Nunclon, Nunc), followed by reaction at room temperature for 30 minutes. After addition of 100 µl of 0.2N hydrochloric acid, the mixture was immersed in boiling water for 2.5 minutes, and cyclic adenosine monophosphate (cAMP) produced by a PTH receptor was extracted from the cells. The total cAMP in the culture solution and the cells was assayed using a commercial radioimmunoassay kit (cyclic AMP [$^{125}$I] kit "Du Pont-Daiichi", Daiichi Kagaku Yakuhin). An increase in cAMP production depending on the concentration of the human PTH partial peptide (the 1–34 positions) added as a standard was always observed. hPTH obtained in Example 1 described above also had an activity approximately similar to this activity (refer to FIG. 11).

The hPTH gene provided by the present invention has the novel DNA sequence and shows a high expression rate of hPTH. Further, the present invention first made it possible to allow hPTH to express in large amounts in the system using *E. coli* as the host. Furthermore, hPTH can be produced more efficiently by the recombinant DNA technique of the present invention using the synthetic gene corresponding to hPTH, which serves to produce hPTH as a therapeutic agent or to study the biological role of hPTH in vivo.

What is claimed is:
1. Plasmid pE-PTH.
2. An *Escherichia coil* transformed with plasmid pE-PTH.
3. A method for producing human parathyroid hormone which comprises cultivating an *Escherichia coli* transformed with plasmid pE-PTH under conditions suitable for expression of said human parathyroid hormone and recovering the same.

* * * * *